United States Patent [19]

Leight

[11] Patent Number: 5,724,119
[45] Date of Patent: Mar. 3, 1998

[54] EARMUFF-EYEGLASS COMBINATION

[75] Inventor: Howard S. Leight, Santa Monica, Calif.

[73] Assignee: Howard S. Leight & Associates Inc., San Diego, Calif.

[21] Appl. No.: 683,515

[22] Filed: Jul. 12, 1996

[51] Int. Cl.$^6$ ................... G02C 1/00; G02C 5/14
[52] U.S. Cl. ........................... 351/158; 351/119
[58] Field of Search .................... 351/119, 158, 351/155, 41, 111, 121, 118; 2/448, 431, 449, 209

[56] References Cited

U.S. PATENT DOCUMENTS

| | | | |
|---|---|---|---|
| 264,574 | 9/1882 | Shore | 351/119 |
| 3,030,627 | 4/1962 | Rehman . | |
| 3,943,925 | 3/1976 | Leight . | |
| 3,946,466 | 3/1976 | Sakai . | |
| 4,259,747 | 4/1981 | Taesler . | |
| 4,802,243 | 2/1989 | Griffiths . | |
| 4,856,089 | 8/1989 | Horton . | |
| 5,133,596 | 7/1992 | Korny . | |
| 5,252,069 | 10/1993 | Lamb et al. . | |
| 5,278,999 | 1/1994 | Brown . | |
| 5,353,071 | 10/1994 | Bradshaw . | |
| 5,373,583 | 12/1994 | Birum . | |

*Primary Examiner*—Hung X. Dang
*Attorney, Agent, or Firm*—Freilich Hornbaker Rosen

[57] ABSTRACT

A combination of earmuff and eyeglass assemblies (12, 14) are provided, that facilitate adjustment of the position of the eyeglass (40) on the wearer and the raising and lowering of the eyeglass, in a construction that avoids interference with movement of the earmuffs (20, 22) against each other. The eyeglass assembly includes a pair of temple bar devices (46, 48) that each comprises two pivotally connected bars (50, 52), with the first bar having a rear end (56) pivotally mounted on a top portion (134) of an earmuff shell (24), and with the second bar pivotally connected about horizontal and vertical axes (74, 81) to one side of the eyeglass. A ball-and-socket coupling (80) is mounted on the top portion of each earmuff shell, with each socket (102) having a vertical slot portion (110) that allows the temple bar devices to be pivoted up and down, and with each socket having a horizontal slot portion (112) that allows the earmuffs to move together. As the front end of the first bar starts to pivot down from a raised position, it lies in slight interference fit with a portion (104) of the socket, so the temple bar device tends to remain raised until firmly pushed down.

9 Claims, 3 Drawing Sheets

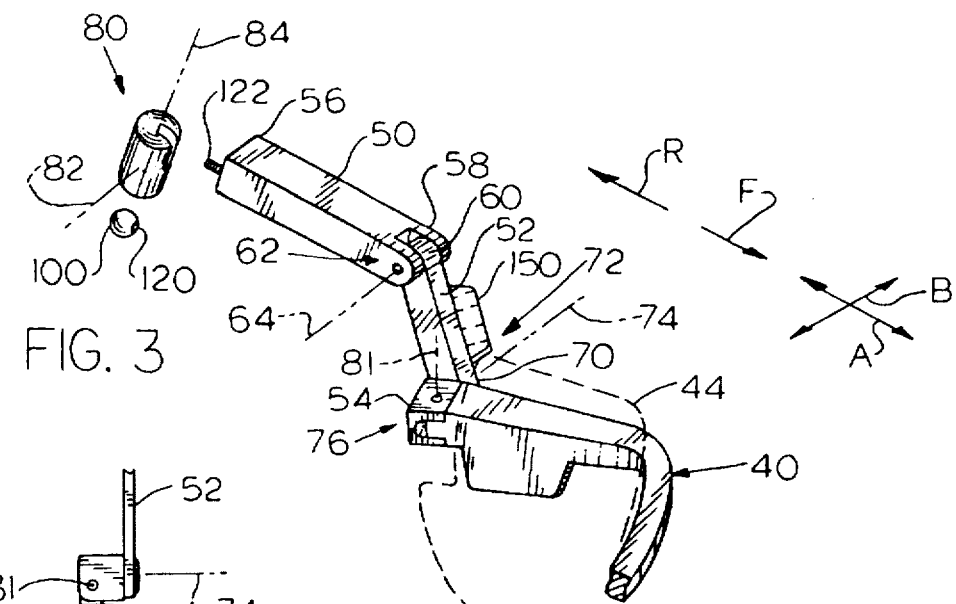
FIG. 3
FIG. 4A
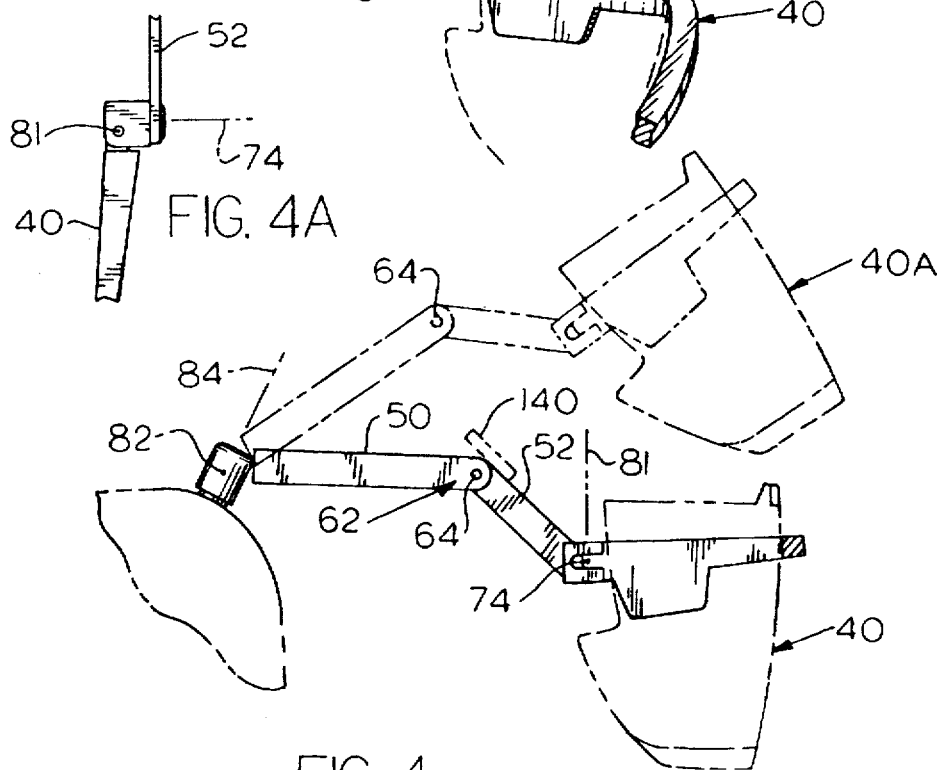
FIG. 4
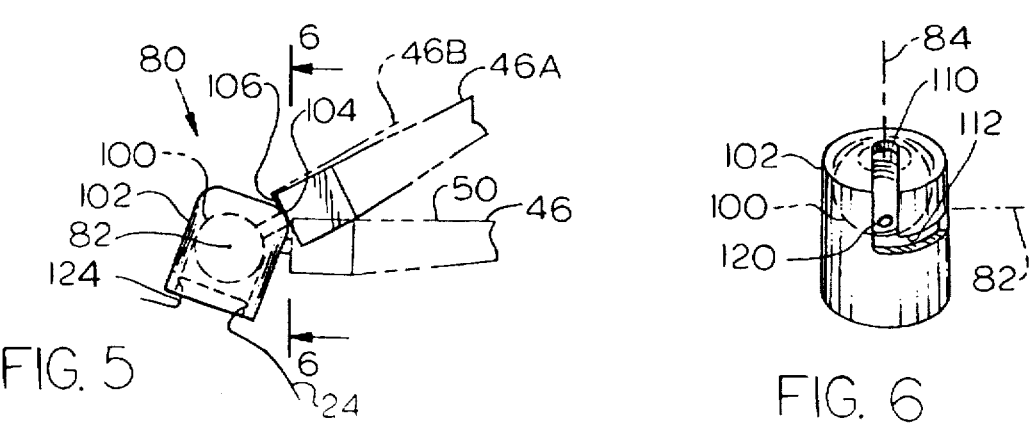
FIG. 5
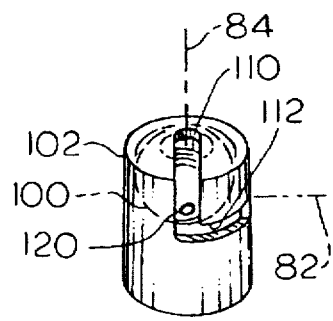
FIG. 6

EARMUFF-EYEGLASS COMBINATION

DESCRIPTION OF THE PRIOR ART

It is known to mount eyeglasses on apparatus that fits on the head of a wearer, such as earmuffs, helmets, or masks. Especially in the case of earmuffs, it is common to mount the eyeglasses so they can be raised to enable a person to directly see an object and then lowered for eye protection. It is also common to provide forward-to-rearward adjustment of the eyeglasses on the earmuffs, so the eyeglasses fit closely in front of the wearer's face for comfort and effective protection. U.S. Pat. No. 5,278,999 shows a prior art structure wherein the opposite sides of the eyeglass can be slid forward and rearward on temple bars for proper positioning for a person, and the rear ends of the temple bars are pivotally mounted at the inner sides of the earmuff shells to enable the eyeglasses to be raised and lowered. Adjustment of the eyeglass position by sliding along the temple bars and pivoting of the temple bars, relies on sliding friction for forward-rearward movement and pivoting for a proper tilt angle, and it is sometimes difficult to achieve about the same resistance to sliding and tilt so they are both easily accomplished at the same time.

The earmuffs are mounted on bands that press against the wearer's ears, and when not worn the earmuffs tend to move against each other. Such movement could deform the temple bars unless provisions are made for it. A system for mounting eyeglasses on head-mounting devices, especially earmuffs, which enabled adjustment of eyeglasses in forward-rearward position and tilt, always with moderate resistance, and which allowed earmuffs to move close together without bending the eyeglass temple bars, would be of value.

SUMMARY OF THE INVENTION

In accordance with one embodiment of the present invention, an eyeglass assembly is provided for mounting on an apparatus such as an earmuff assembly that fits on the head of a wearer, which facilitates adjustment of an eyeglass and which permits earmuffs to move together when not worn. In a combination of eyeglass and earmuff assemblies, a pair of temple bar devices that support an eyeglass, each has a plurality of bars. The bars include a first bar with a rear end pivotally connected to the earmuff assembly, preferably about horizontal and vertical axes. A second bar has a rear end pivotally connected to the first bar about a horizontal axis and a front end pivotally coupled to a corresponding side of the eyeglass, preferably about horizontal and vertical axes. The pivotal coupling of the second bar to the eyeglass about two axes, can be through a third bar that serves as a universal coupling that permits two axes of pivoting.

The two-axis coupling of the rear end of each temple bar device to an earmuff, is preferably through a ball and socket joint mounted on the top portion of the earmuff shell. The socket has intersecting vertical and horizontal slots, the vertical slots allowing the eyeglass to be raised to allow the wearer to directly view an object, and the horizontal slots allowing the earmuffs to move close together. The outside of each socket is constructed for slight interference fit with a corresponding temple bar, as a temple bar begins to be lowered from a raised position.

The novel features of the invention are set forth with particularity in the appended claims. The invention will be best understood from the following description when read in conjunction with the accompanying drawings.

BRIEF DESCRIPTION OF THE DRAWINGS

FIG. 3 is a partially exploded isometric view of one temple bar device and a portion of the eyeglass, and of means for mounting the temple bar device on an earmuff.

FIG. 4 is a side elevation view of a portion of the combination of FIG. 2, showing the eyeglass assembly in lowered and raised positions.

FIG. 4A is a plan view of a portion of the eyeglass assembly of FIG. 4.

FIG. 5 is a view of a portion of the combination of FIG. 4, showing the temple bars in the two positions of FIG. 4, and also in a third position.

FIG. 6 is a view taken on line 6—6 of FIG. 5.

DESCRIPTION OF THE PREFERRED EMBODIMENT

Figure 1:
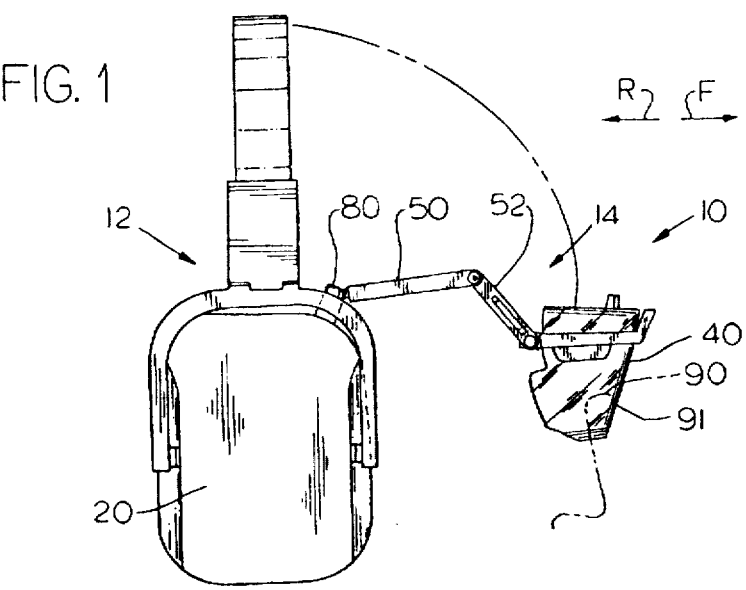
FIG. 1 is a side elevation view of an eyeglass assembly constructed in accordance with the present invention, shown mounted on an earmuff assembly, and with both assemblies being mounted in a use position on a person's head.

FIG. 1 illustrates a combination 10 of an earmuff assembly 12 and an eyeglass assembly 14. The combination is useful to protect both the ears and eyes of the wearer, as when the wearer is in a noisy environment and is operating machinery that could throw off particles that could injure the wearer's eyes. Another environment is when the wearer is practicing shooting a gun.

Figure 2:
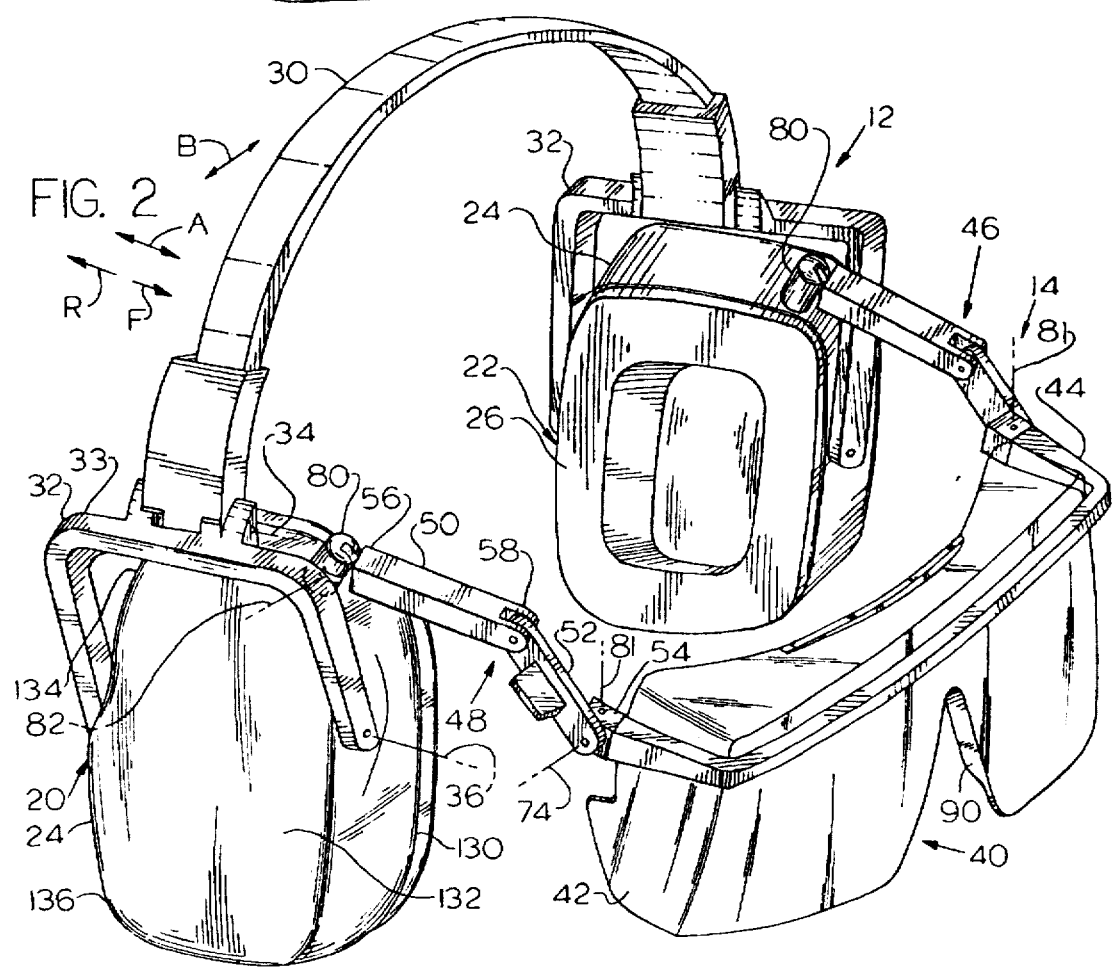
FIG. 2 is an isometric view of the combination of FIG. 1, shown in the use position of FIG. 1, but without showing the head of the wearer.

As shown in FIG. 2, the particular earmuff assembly shown includes a pair of earmuffs 20, 22 that each includes a rigid shell 24 and a soft cushion 26. The earmuffs are connected through a resilient band 30 whose opposite ends are pivotally connected to yokes 32, with each yoke pivotally connected to an earmuff shell. The yokes are pivotally connected about axis 34, 36 which extend in longitudinal directions A which are parallel to forward and rearward directions F, R.

The eyeglass assembly 14 includes an eyeglass 40 having right and left sides 42, 44 spaced apart in a lateral direction B which is substantially perpendicular to direction A. The opposite sides of the eyeglass are mounted on the earmuffs by left and right temple bar assemblies 46, 48. As shown in FIG. 3, each temple bar assembly includes first, second, and third bars 50, 52, 54 that are pivotally connected in series, and to one of the earmuffs and one side of the eyeglass. The first bar has a rear end 56 that is pivotally connected to the earmuff, and has a front end 58. The second bar has a rear end 60 pivotally connected to the front end of the first bar at a pivot joint 62 that permits relative pivoting about a largely horizontal laterally-extending axis 64. The second bar has a front end 70 that is pivotally connected to the third bar at a joint 72 that permits pivoting about a laterally-extending axis 74. The third bar is pivotally connected to one side of the eyeglass to permit relative pivoting at a third joint 76 that permits pivoting about a vertical axis 81. Thus, the third bar serves as a two-axis joint. The rear end 56 of each first bar is pivotally connected to an earmuff shell through a coupling 80 that permits pivoting about a lateral axis 82 to raise the eyeglass above the wearer's eyes and move them down in front of his eyes. The coupling 80 also permits pivoting about another axis 84 that is largely vertical, although it is inclined about 30° from the vertical.

The first and second bars 50, 52 are elongated, with the first bar 50 having a length (between axes 82, 64) of about 45 mm and the second bar 52 having a length of about 30 mm. It would be possible to provide an additional elongated bar lying between and coupled to the first and second bars, although applicant finds that sufficient flexibility is obtained with only two elongated bars. The third bar 54 is short, and the two pivot axes 74, 81 are only a few millimeters apart or can even intersect. The third bar 54 essentially serves as a "universal joint" that permits pivoting about two axes. Although a ball and socket joint could be used instead of the bar 54, applicant prefers to use the bar. Also, instead of using a ball and socket joint at the coupling 80, it would be possible to use a universal joint with two separate pivot axes. All of the horizontal axes of pivoting 82, 64, 74 are substantially parallel.

The presence of relatively long bars 50, 52 that are pivotally connected together and at their opposite ends, enables the eyeglass 40 to be moved forward and rearward and to be tilted about horizontal axes, to comfortably position the eyeglass for a particular wearer. For most wearers, the comfortable position of the eyeglass 40 shown in FIG. 1, is with a nose mount 90 resting against a location near the top of the nose, and with the front 91 of the eyeglass directed at a slight downward angle. The temple bar devices with pivoting bars permits such adjustment, with the adjustments being made by pivoting, and with the resistance to pivoting being closely controllable as compared to sliding friction. Applicant prefers to produce moderate resistance to pivoting at the axes 64, 74, as where a torque of two inch pounds is required to pivot the bars thereat. A lower friction is provided for pivoting at the axis 82 on an earmuff, so the eyeglass tends to rest on the wearer's nose, although with only a small force. As a result, once the wearer has "set" the position and orientation of the eyeglass 40, the temple bar devices tend to not pivot except about the axis 82, in raising and lowering the eyeglass as in FIG. 4.

FIG. 4 shows the eyeglass in a lowered position 40 and in a raised position 40A. A wearer will often raise the eyeglass to the position 40A, to more clearly see a workpiece or a target when there is no danger to his eyesight. As shown in FIG. 5, the coupling 80 includes a ball 100 and socket 102. The socket 102 is fixed to an earmuff shell 24, and the ball can pivot within the socket. When the temple bar device 46 is fully raised to the position 46B, the weight of the eyeglass tends to pivot it down towards the lower position 46. The outside of the socket 102 contains a barrier at 104 that interferes with a surface 106 at the rear end of the first bar as the temple bar device and first bar 50 thereof move from a fully upward position 46B to a slightly lower raised position 46A. As a result, the eyeglass tends to remain in the raised position 46A. However, when a downward torque of about one inch pound is applied, the eyeglass assembly will pass the barrier 104 and thereafter tend to pivot down until stopped by the nose of the wearer. Because of the lower resistance to pivoting at 80, downward force applied to the eyeglass assembly to pivot it down to its lowered position, does not tend to change the "setting" at which the joints 62, 76 at axes 64, 74 tend to remain.

As shown in FIG. 6, the socket 102 has a vertical slot portion 110 which extends with vertical directional components, to permit the temple bar to pivot about the lateral axis 82 to raise or lower the eyeglass assembly on the wearer. The socket also has a horizontal slot portion 112 that intersects the vertical slot. The horizontal slot portion 112 permits the corresponding temple bar device to pivot about the largely vertical axis 84. Pivoting about the largely vertical axis 84 is desirable in avoiding bending of the temple bars when the earmuffs move together. The slot portions each extends on the order of 90° about the center of the ball, to avoid substantial weakening of the socket. When the temple bars are raised, the vertical slot portion 110 helps avoid pivoting of the eyeglass assembly far to the left or right.

Figure 7:
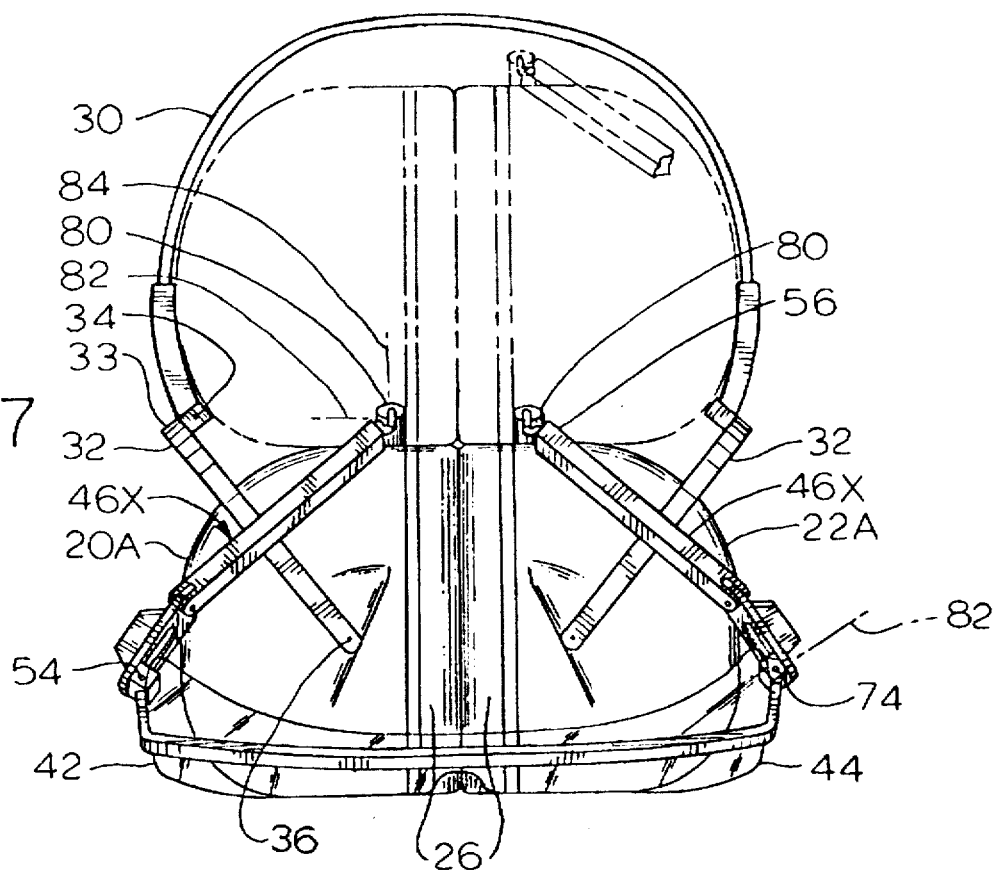
FIG. 7 is a front elevation view of the combination of FIG. 2, in a partially stowed position, and showing, in phantom lines, the combination in a fully stowed position.

FIG. 7 shows that the band 30 that joins the earmuffs, tends to move the earmuffs at 20A, 22A close together, which may even result in the soft cushions 26 of the earmuffs pressing against each other. The band 30 is constructed in this way to assure that the earmuffs will press firmly against the opposite sides of the wearer's head, to assure good sound protection. When the earmuffs move together, the temple bar devices move to the positions 46X, 48X wherein the rear ends 56 of the first bars are much closer together than the opposite sides 42, 44 of the eyeglass. This configuration of the temple bar devices is permitted by their pivoting about the largely vertical axes 82, 54.

Referring to FIG. 3, it can be seen that the ball 100 of the coupling 80 has a threaded hole 120, and the first bar rear end has a threaded stud 122. To assemble the coupling 80, the ball 100 is first inserted into the socket. Then the threaded stud 122 is screwed into the ball. In a later version, applicant has molded the ball in place in the socket, with the ball being integral with the first bar rear end. FIG. 5 shows the socket 102 held to a mount 124 that is mounted on the earmuff shell 24. FIG. 2 shows that each earmuff shell has inner and outer sides 130, 132 and top and bottom portions 134, 136. Each coupling 80 is preferably mounted on a top portion 134 between the inner and outer sides. When the earmuffs are close together, the resilient band 30 moves the tops 33 of the yokes 32 away from each other. As a result, even though the temple bar devices 46, 48 diverge with their front ends furthest apart, when the earmuffs are together there is no interference with the yokes 32. On the other hand when the earmuffs are spread apart, when worn on a person's head, the upper ends of the yokes move together, but the temple bar devices then tend to extend parallel and in the longitudinal direction. Mounting of the temple bar rear ends on the top portions of the earmuff shells, results in the first and second bars 50, 52 having an orientation such as shown in FIG. 1, wherein the second bar 52 extends at a downward-forward incline, and can be readily pivoted to move the eyeglass forward or rearward. If the couplings 80 were located at the bottom portion of the earmuff, then the temple bars might interfere with the cheeks of the wearer, and if they were located halfway between the top and bottom then the first bar 50 would have to extend at an upward incline to allow the second bar 52 to extend at a downward incline, which would lengthen the temple bar devices and result in interference with the earmuff assembly yokes 32.

As indicated in FIG. 4, applicant prefers to provide stops 140 at the joint 62 where the first and second bars 50, 52 are pivotally connected. The stop 140 prevents the bars 50, 52 from pivoting further than a position of alignment; that is, it prevents the second bar 52 from extending at an upward incline from the first bar 50 when the first bar 50 extends horizontally. The stop 140 assures that both second bars 52 will extend at a downward incline, instead of having a first bar on one side extending at a downward incline and a first bar on the other side extending at an upward incline, which skews the eyeglass. Applicant also prefers to provide handles 150 (FIG. 3) on the second bars. This encourages the wearer to lift and lower the eyeglasses by raising and lowering the handles 52. The handles 52 are located so they minimize the possibility of pivoting at the joints 62, 74 when the rear ends of the temple bar devices pivot on the shells.

Thus, the invention provides an eyeglass assembly for mounting on an apparatus that fits on the head of a wearer, and the combination of the eyeglass assembly with an earmuff assembly, which facilitates adjustment of the eyeglass so it fits comfortably in position and orientation on the wearer, which permits raising and holding up of the eyeglass without changing the "setting" of the eyeglass in its downward position, and which permits the earmuffs to move together without bending the temple bar devices. Each temple bar device has front and rear ends pivotally connected about a largely horizontal axis with respect to a side of the eyeglass and with respect to an earmuff. Each temple bar device includes at least two elongated bars that are pivotally connected, to allow adjustment of the front-to-rear position of the eyeglass by pivoting of the bars. The rear ends of the temple bars are preferably mounted on upper portions of the earmuff shells, and preferably can pivot about largely vertical axes as well as horizontal axes. Pivoting about largely vertical axes permits the earmuffs to move close together while the opposite sides of the eyeglass remain laterally spaced far apart. The temple bar devices are preferably mounted on the earmuff shells by a ball and socket joint, with each socket having vertical and horizontal slots that intersect.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A combination that includes an earmuff assembly and an eyeglass assembly, where the eyeglass assembly includes an eyeglass with opposite sides and a pair of temple bar devices, and where each temple bar device has a rear end pivotally mounted on said earmuff assembly and has a front end coupled to a corresponding side of said eyeglass, wherein:

each of said temple bar devices includes a plurality of bars, including a first bar having a rear end pivotally connected to said earmuff assembly and having a front end lying forward of said rear end, and a second bar having a rear end pivotally connected to said front end of said first bar and having a front end which lies forward of said second bar rear end and which is pivotally coupled to a corresponding side of said eyeglass, whereby to enable adjustment of the forward-rearward position of the eyeglass.

2. The combination described in claim 1 wherein:

said first bar rear end is pivotally connected to said earmuff at a first joint, said first and second bars are pivotally connected at a second joint, and the front end of said second bar is pivotally coupled to said eyeglass at a third joint, with said first, second, and third joints each allowing pivoting about a substantially horizontal axis;

the friction at said second joint and at said third joint are each great enough compared to the pivot friction at said first joint, that when an upward or downward force is applied to said eyeglass there is pivoting only at said first joint, whereby to avoid change in a setting for an individual.

3. An eyeglass assembly for mounting on apparatus that fits on the head of a wearer, including a pair of earmuffs and a band that connects said earmuffs and that biases said earmuffs toward each other, comprising:

an eyeglass with opposite sides;

a pair of temple bar devices that each has a rear end for mounting on said apparatus that fits on the head of a wearer and a front end for mounting on a side of said eyeglass, with each of said temple bar devices having a plurality of pivotally connected bar means connected at pivot joint means for adjusting the distance between the temple bar device rear and front ends primarily by pivoting at said plurality of pivot joint means, with said bar means comprising first and second bars with the front end of said first bar and the rear end of said second bar being pivotally connected to permit pivoting about a primarily horizontal axis;

for each of said temple bar devices, said first bar rear end is connected to one of said earmuffs in a joint that permits pivoting of said first bar about a primarily vertical axis and about a primarily horizontal axis, and said second bar front end is connected to a side of said eyeglass in a joint that permits pivoting of said side of said eyeglass about a primarily vertical axis and about a primarily horizontal axis.

4. An eyeglass assembly, comprising:

apparatus that fits on the head of a person and that includes a pair of earmuffs and a band that joins said earmuffs, with each earmuff including a hard shell that has opposite inner and outer sides, top and bottom shell portions, and a soft compressible cushion mounted on said shell inner side for compression against a wearer's ear;

an eyeglass with opposite sides;

a pair of temple bar devices that each has a rear end for mounting on said apparatus that fits on the head of a wearer and a front end for mounting on a side of said eyeglass, with each of said temple bar devices having a plurality of pivotally connected bar means connected at pivot joint means for adjusting the distance between the temple bar device rear and front ends primarily by pivoting at said plurality of pivot joint means;

each of said temple bar device rear ends is connected to one of said shell top portions in a joint that allows the temple bar rear end to pivot about a largely horizontal axis and about a largely vertical axis with respect to said shell.

5. A combination that includes an earmuff assembly and an eyeglass assembly, where the eyeglass assembly includes an eyeglass with opposite sides and a pair of temple bar devices, and where each temple bar device has a rear end pivotally mounted on said earmuff assembly and has a front end coupled to a corresponding side of said eyeglass, wherein:

each of said temple bar devices includes a plurality of bars, including a first bar having a rear end pivotally connected to said earmuff assembly and having a front end, and a second bar having a rear end pivotally connected to said front end of said first bar and having a front end pivotally coupled to a corresponding side of said eyeglass, whereby to enable adjustment of the forward-rearward position of the eyeglass;

said second bar rear end is pivotally connected to said first bar about a substantially horizontal axis, and including a stop that prevents said second bar from pivoting in a first direction past an alignment position wherein said first and second bars are substantially aligned with their ends lying substantially along a straight line, wherein pivoting in said first direction past said alignment position would raise said second bar front end.

6. A combination that includes an earmuff assembly and an eyeglass assembly, where the eyeglass assembly includes an eyeglass with opposite sides and a pair of temple bar devices, and where each temple bar device has a rear end pivotally mounted on said earmuff assembly and has a front end coupled to a corresponding side of said eyeglass, wherein:

each of said temple bar devices includes a plurality of bars, including a first bar having a rear end pivotally connected to said earmuff assembly and having a front end, a second bar having a rear end pivotally connected to said front end of said first bar and having a front end, and a third bar which is pivotally connected to said second bar front end about a substantially horizontal axis, and which is pivotally connected to a side of said eyeglass about a substantially vertical axis.

7. A combination that includes an earmuff assembly and an eyeglass assembly, where the eyeglass assembly includes an eyeglass with opposite sides and a pair of temple bar devices, and where each temple bar device has a rear end pivotally mounted on said earmuff assembly and has a front end coupled to a corresponding side of said eyeglass, wherein:

each of said temple bar devices includes a plurality of bars, including a first bar having a rear end pivotally connected about a largely horizontal first axis on said earmuff assembly and having a front end, and a second bar having a rear end pivotally connected to said front end of said first bar and having a front end pivotally coupled to a corresponding side of said eyeglass;

said first bar rear end has a first interference part that moves along a circle as said first bar pivots about said first axis on said earmuff, and said earmuff has a second interference part that is positioned to interfere with movement of said first interference part as said first bar pivots down past a raised position while allowing such downward pivoting when a moderate downward torque is applied to said first bar, to keep the eyeglass raised above the wearer's eyes until the eyeglass is forced down.

8. A combination that includes an earmuff assembly comprising a pair of earmuffs and an eyeglass assembly, where the eyeglass assembly includes an eyeglass with opposite sides and a pair of temple bar devices, and where each temple bar device has a rear end pivotally mounted on said earmuff assembly and has a front end coupled to a corresponding side of said eyeglass, wherein:

each of said temple bar devices includes a plurality of bars, including a first bar having a rear end pivotally connected to said earmuff assembly and having a front end, and a second bar having a rear end pivotally connected to said front end of said first bar and having a front end pivotally coupled to a corresponding side of said eyeglass; and including a coupling mounted on each of said earmuffs and connecting a first bar rear end of a corresponding temple bar device to the earmuff, wherein each of said couplings includes a socket mounted on one os said earmuffs and having a slot, and a ball member rotatably held within the socket, with the ball connected to the rear end of a corresponding one of said first bars through said slot.

9. The combination described in claim 8 wherein said earmuff assembly includes a band that connects said earmuff and that biases said earmuff toward each other, and wherein:

the socket and ball of each coupling have substantially coincident centers, and each of said sockets has a largely vertically-extending slot portion that extends by an angle on the order of 90° about a substantially horizontal axis that passes through said center, and each of said sockets has a largely horitzontally-extending slot portion that extends on the order of 90° about a substantially vertical axis and that intersects said vertically-extending slot portion.

* * * * *